United States Patent
Nakazawa

(10) Patent No.: US 9,826,952 B2
(45) Date of Patent: Nov. 28, 2017

(54) X-RAY CT APPARATUS AND SCANNING METHOD

(71) Applicant: HITACHI, LTD., Tokyo (JP)

(72) Inventor: Tetsuo Nakazawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 14/891,981

(22) PCT Filed: May 15, 2014

(86) PCT No.: PCT/JP2014/062902
§ 371 (c)(1),
(2) Date: Nov. 18, 2015

(87) PCT Pub. No.: WO2014/188937
PCT Pub. Date: Nov. 27, 2014

(65) Prior Publication Data
US 2016/0095566 A1   Apr. 7, 2016

(30) Foreign Application Priority Data
May 24, 2013   (JP) .................................. 2013-109464

(51) Int. Cl.
*A61B 6/00*   (2006.01)
*A61B 6/03*   (2006.01)

(52) U.S. Cl.
CPC ............ *A61B 6/5217* (2013.01); *A61B 6/032* (2013.01); *A61B 6/50* (2013.01); *A61B 6/501* (2013.01); *A61B 6/504* (2013.01)

(58) Field of Classification Search
CPC ....... A61B 6/032; A61B 6/542; G01N 23/046
See application file for complete search history.

(56) References Cited

U.S. PATENT DOCUMENTS

2014/0177803 A1\* 6/2014 Stevens .................... A61B 6/52
378/98

FOREIGN PATENT DOCUMENTS

| JP | 2007215642 A | 8/2007 |
| JP | 2009060939 A | 3/2009 |

(Continued)

OTHER PUBLICATIONS

Kazuyuki Abe et al., "Ai ni Okeru Shinryo Hoshasen Gishi no Yakuwari—X-Sen CT Satsuzo to no Guideline—(Innai Ai Jisshi Hen)", Mar. 31, 2010 (Mar. 31, 2010), Shadan Hojin Nippon Hoshasen Gishikai, Internet <URL:http://www.jart.jp/news/documents.html>.

(Continued)

*Primary Examiner* — Hoon Song

(57) ABSTRACT

To provide an X-ray CT apparatus and a scanning method that can scan a corpse efficiently, a death mode is selected and input to the CPU of an image processing device by performing a mouse-click or touch operation on any of buttons on a death mode selection window. The CPU obtains scanning conditions from the storage unit according to the input death mode. In a charred body mode, scanning conditions are defined in advance to perform high-resolution scanning for the pelvis portion and standard scanning for the other entire body for sex estimation. The sex estimation process estimates the corpse's sex based on the pelvis portion shape and outputs the results. In a drowned body mode, scanning conditions are defined in advance to perform high-resolution scanning for the lung field and standard scanning for the other entire body to measure a water amount in the lung.

9 Claims, 16 Drawing Sheets

(56) References Cited

FOREIGN PATENT DOCUMENTS

JP          2012090923 A      5/2012
WO    WO 2008/140101      * 10/2008

OTHER PUBLICATIONS

Haruo Saito et al., "Hoi Kaibo Mae Ct no Yuyosei—Sanjigen Gazo ga Shindan ni Kiyo shita Rei o Chushin ni", Inner Vision, Dec. 25, 2012 (Dec. 25, 2012), vol. 28, No. 1, pp. 50 to 53.
Pomara C, et al., Virtopsy versus digital autopsy: virtual autopsy, Radiologia Medica, 2009, vol. 114, No. 8, pp. 1367-1382.
Christina Jacobsen, et al., Craniocerebral trauma—Congruence between post-mortem computed tomography diagnoses and autopsy results: A 2-year retrospective study, Forensic Science International, 2010, vol. 194, pp. 9-14.
PCT/JP2014/062902 International Search Report dated Jun. 24, 2014.

* cited by examiner

FIG. 4

8 SCANNING CONDITIONS BY DEATH MODE 

| SCANNING MODE | STANDARD SCANNING | HIGH-RESOLUTION SCANNING | STANDARD SCANNING CONDITIONS | HIGH-RESOLUTION SCANNING CONDITIONS |
|---|---|---|---|---|
| 1. CHARRED BODY | WHOLE BODY | PELVIS PORTION | 120kV,100mA 1.2mmslice, Pitch 1.2 | 120kV,300mA 0.625mmslice |
| 2. DROWNED BODY | WHOLE BODY | LUNG FIELD | 120kV,100mA 1.2mmslice, Pitch 1.2 | 120kV,300mA 0.625mmslice |
| 3. HEAD INJURY | WHOLE BODY | HEAD PORTION | 120kV,100mA 1.2mmslice, Pitch 1.2 | 120kV,200mA 0.625mmslice |
| 4. THORACO-ABDOMINAL INJURY | WHOLE BODY | THORACOABDOMINAL PORTION | 120kV,100mA 1.2mmslice, Pitch 1.2 | 120kV,300mA 0.625mmslice |
| 5. HEAD DISEASE | WHOLE BODY | HEAD PORTION | 120kV,100mA 1.2mmslice, 1.2 | 120kV,200mA 0.625mmslice |
| 6. HEART DISEASE | WHOLE BODY | HEART | 120kV,100mA 1.2mmslice, Pitch 1.2 | 120kV,200mA 0.625mmslice |
| 7. OTHERS | WHOLE BODY | WHOLE BODY | 120kV,100mA 1.2mmslice, Pitch 1.2 | |

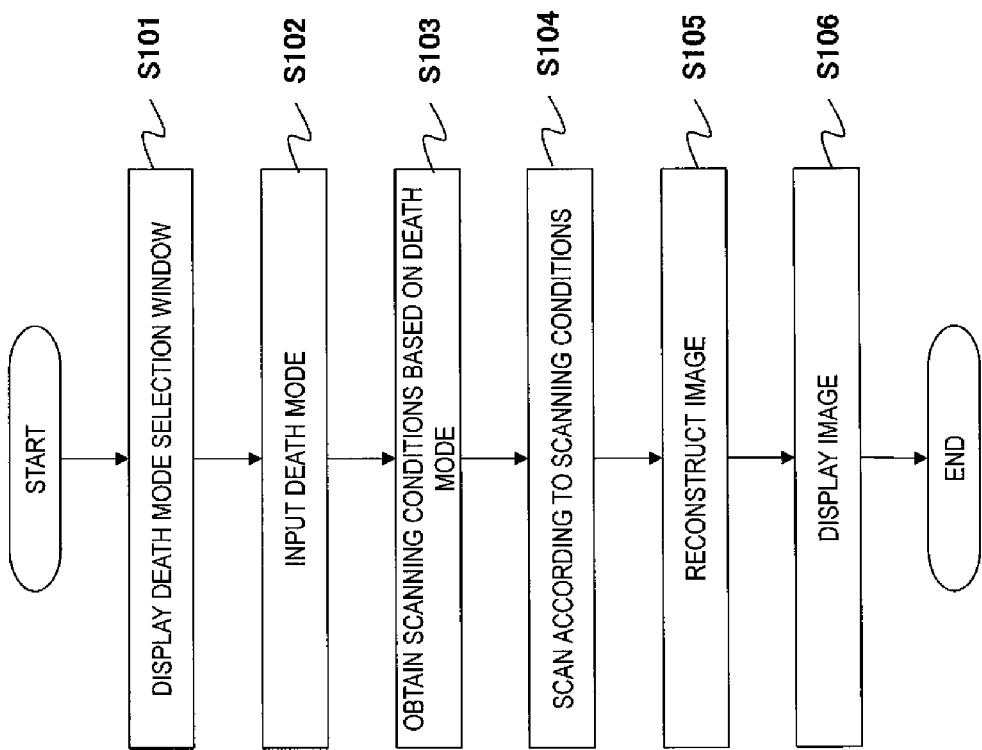

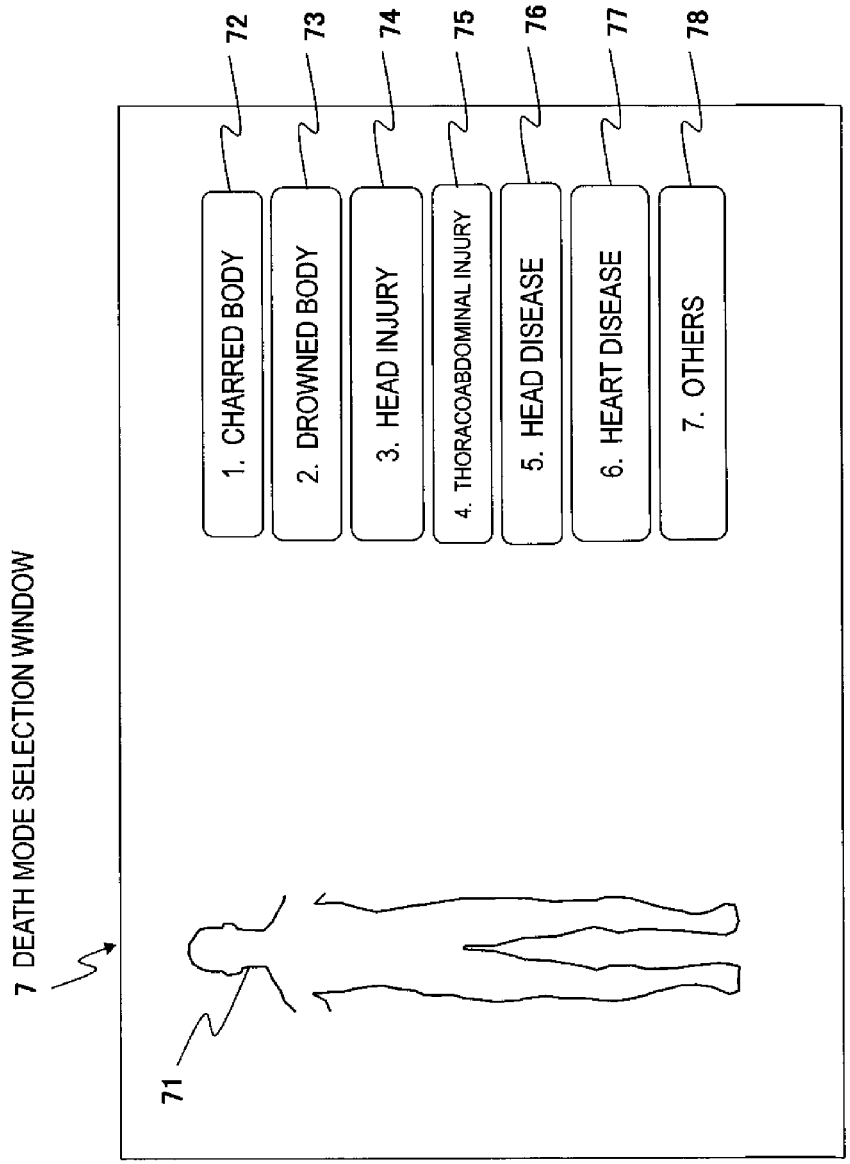

FIG. 10
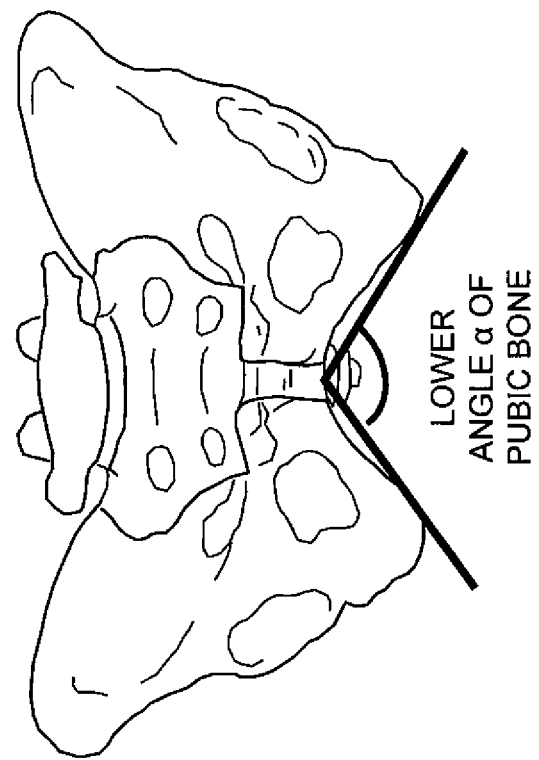
(a) MALE
LOWER ANGLE α OF PUBIC BONE
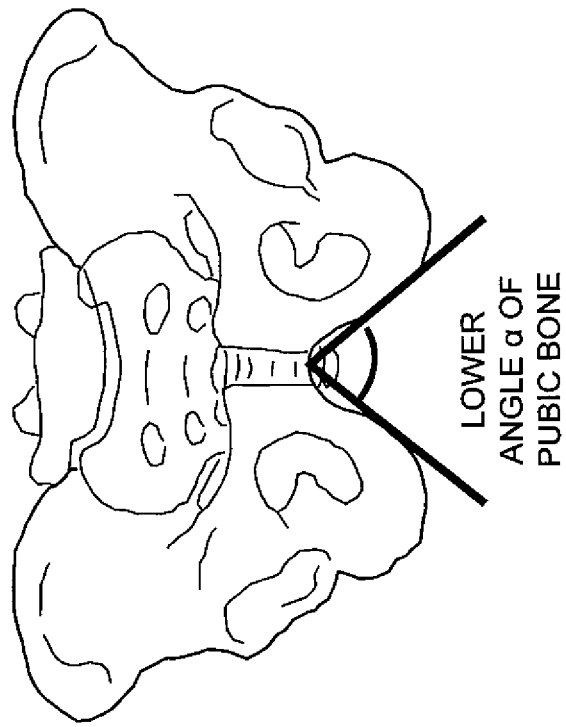
(b) FEMALE
LOWER ANGLE α OF PUBIC BONE

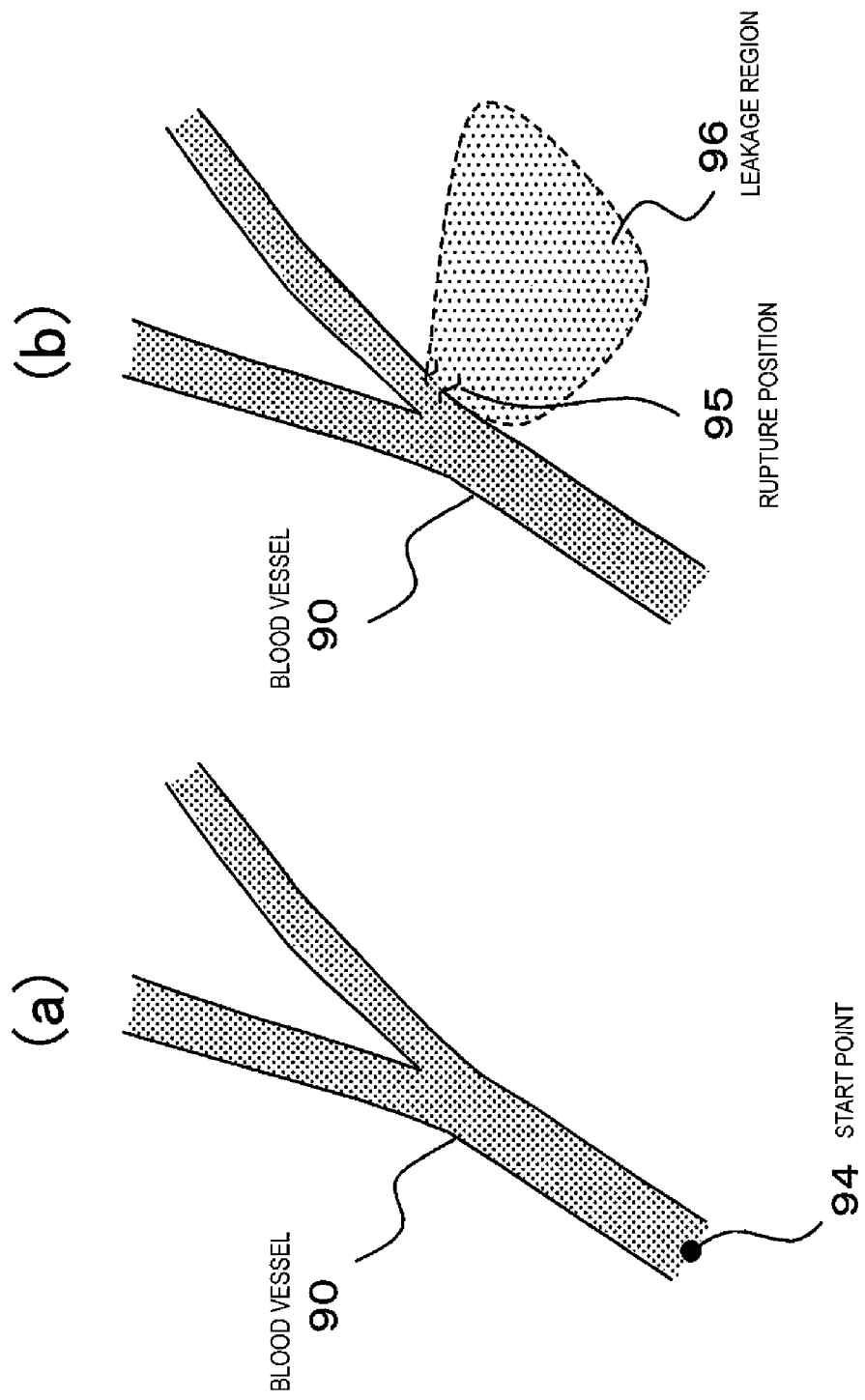

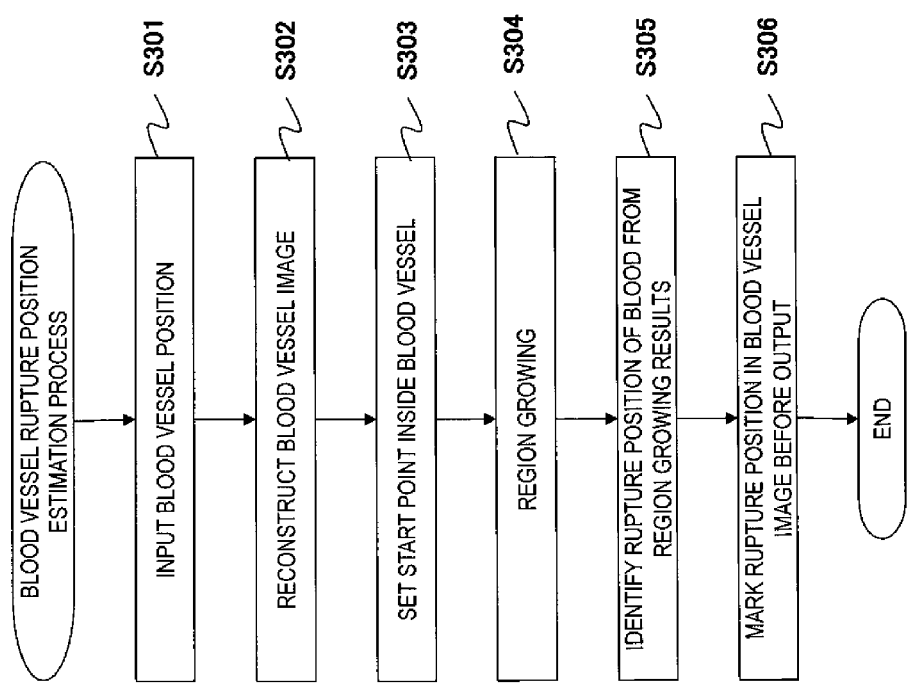

X-RAY CT APPARATUS AND SCANNING METHOD

TECHNICAL FIELD

The present invention relates to an X-ray CT apparatus and a scanning method, and in details, to X-ray CT scanning of a dead human body.

BACKGROUND ART

A conventional medical X-ray CT (Computed Tomography) apparatus has spread widely as an apparatus for scanning a living human body mainly. On the other hand, an X-ray CT apparatus can be used for X-ray CT scanning of a dead human body. This is referred to as AI (Autopsy Imaging) and is construed as an image pathological diagnosis at the time of death in a narrow sense. The AI diagnoses what type of structural disorder is caused in the corpse using an image scanned by an X-ray CT apparatus or MRI apparatus at the time of or after death. The diagnosis results are utilized to understand pathology at the time of death and investigate the cause of death.

By the way, there are insufficient anatomists in the background of the widespread AI using an X-ray CT apparatus. In a case where anatomy is required but is not performed due to the insufficient anatomists, this can result in a wrong cause of death. For example, in a case where a person died with less injury even if there are a rupture of organ and a bone fracture by beating, it may be simply determined that the person died of cardiac paralysis. By scanning the dead body before anatomy using an X-ray CT apparatus or MRI apparatus, organ damage and breeding statuses of various organs as well as whether or not there are bone fractures can be imaged accurately. Therefore, the AI has received a lot of attention as an image diagnosis method that can acquire effective information to determine the cause of death.

Also, it is estimated that a number of corpses are concentratively carried to a local facility in case of a large-scale fire or flood disaster. Particularly, in case of a fire etc., there is a case where even sex cannot be determined depending on the damage degree of a corpse. However, it requires a long time to anatomize all the corpses, which greatly burdens doctors. Even in such a case, the AI scanning is effective.

By the way, it is disclosed that a conventional X-ray CT apparatus converts protocols in which scanning conditions according to the examination site and the examination purpose were defined for a living body in advance into a database and sets the scanning conditions by selecting an appropriate one for the examination from these protocols (Patent Literature 1).

CITATION LIST

Patent Literature

PTL 1: Japanese Unexamined Patent Publication No. 2007-215642

SUMMARY OF INVENTION

Technical Problem

However, since a conventional X-ray CT apparatus is developed in order to scan a living body, it cannot be said that the apparatus is appropriate for scanning a corpse. For example, although it is described that various scanning conditions (protocols) for a living body in each hospital division are converted into a database in PTL 1, protocols specialized for scanning a corpse are not considered. Therefore, various parameters of the scanning conditions needed to be set for each corpse when X-ray CT scanning was performed for a corpse, which could not scan a number of corpses efficiently.

The present invention was made in light of the above problems, and the purpose is to provide an X-ray CT apparatus and a scanning method that can perform scanning for a corpse efficiently.

Solution to Problem

In order to achieve the above purpose, the first invention is an X-ray CT apparatus characterized by comprising: an X-ray source for generating an X-ray; an X-ray detector for detecting an X-ray transmitted through an object; a data acquisition system for acquiring the transmission X-ray data detected by the X-ray detector; a storage unit for storing scanning conditions according to a death mode; an input unit for selecting the death mode by an operator; a scanning controller for reading the scanning condition according to the selected death mode from the storage unit and performing scanning according to the read scanning conditions; and a reconstruction calculator for reconstructing an image according to the death mode using the transmission X-ray data acquired from the data acquisition system during scanning.

Also, the second invention is a scanning method characterized by including: a step of displaying death mode options of on a display device of the X-ray CT apparatus; a step of reading the scanning conditions according to the death mode that was selected from the options by the operator from the storage unit of the X-ray CT apparatus that stored the scanning conditions according to the death mode in advance; a step of performing scanning by the X-ray CT apparatus according to the read scanning conditions; and a step of reconstructing an image according to the death mode by the X-ray CT apparatus using the transmission X-ray data acquired during the scanning.

Advantageous Effects of Invention

The present invention can provide an X-ray CT apparatus and a scanning method that can perform scanning for a corpse efficiently.

BRIEF DESCRIPTION OF DRAWINGS

FIG. 4 is an example of the scanning conditions by death mode 8.

FIG. 5 is a flow chart explaining the flow of the scanning process to be executed by the X-ray CT apparatus 1 related to the present invention.

FIG. 6 is an example of the death mode selection window 7.

FIG. 10 is a schematic diagram showing the shapes of the pelvis portions of a male and female.

FIG. 15 is a diagram explaining the leakage region 96 and the rupture position 95 of the blood vessel 90.

FIG. 16 is a flow chart explaining the flow of the blood vessel rupture position estimation process to be executed by the image processing device 40c.

DESCRIPTION OF EMBODIMENTS

Hereinafter, referring to the attached diagrams, the suitable embodiments of the present invention will be described in detail.

First, referring to FIGS. 1 and 2, the configuration of the X-ray CT apparatus 1 will be described.

Figure 1:
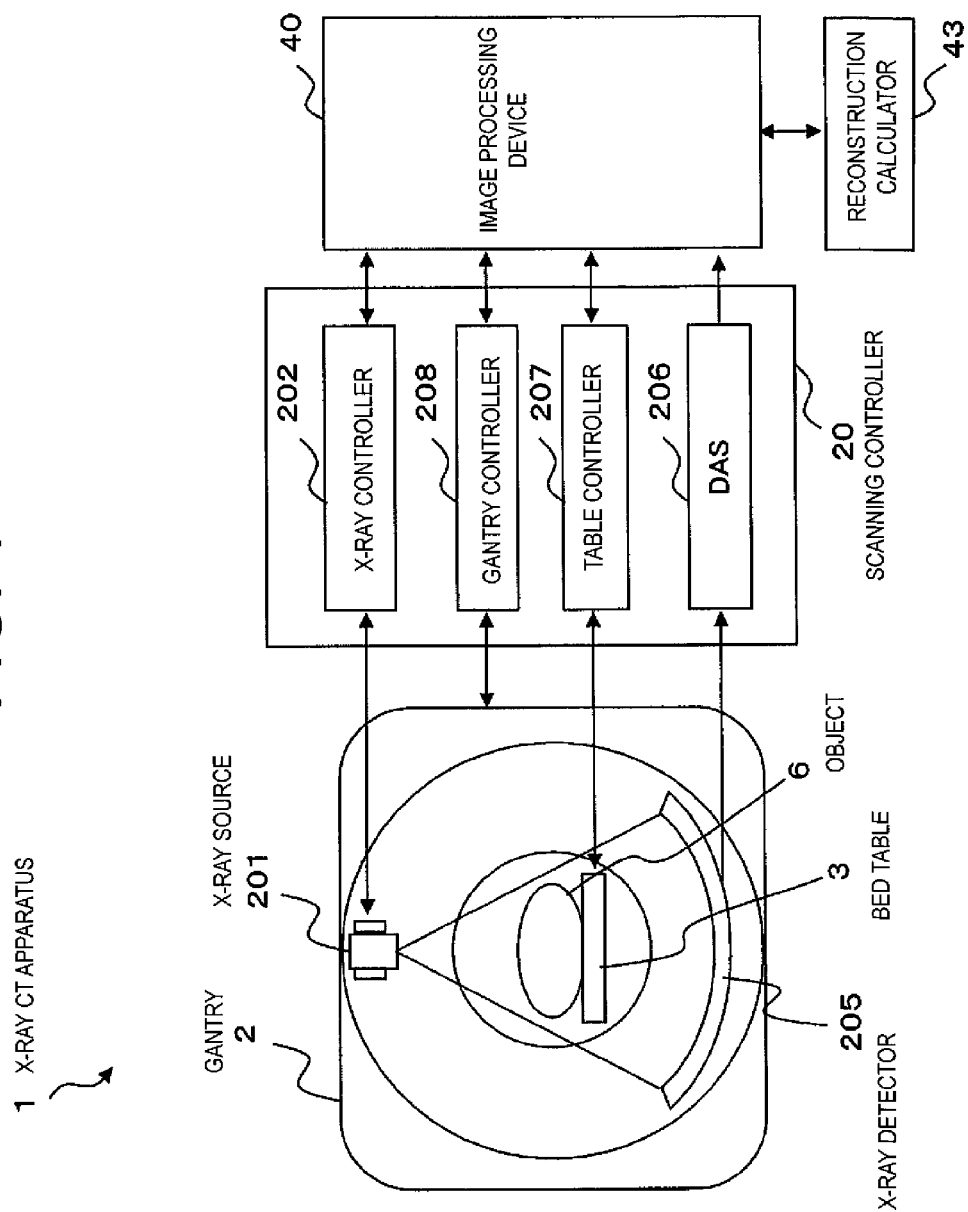
FIG. 1 is an overall configuration diagram of the X-ray CT apparatus 1.

As shown in FIG. 1, the X-ray CT apparatus 1 comprises the gantry 2 for irradiating an X-ray to the object 6 that is a corpse and detecting an X-ray transmitted through the object 6, the bed table 3 for placing the object 6, the image processing device 40 for controlling each part of the X-ray CT apparatus 1, the scanning controller 20 for controlling scanning operations of the gantry 2 according to a control signal to be sent from the image processing device 40, and the reconstruction calculator 43 for reconstructing an image based on the transmission X-ray data acquired by the scanning operations of the gantry 2.

In the gantry 2, the X-ray source 201 and the X-ray detector 205 are oppositely disposed across the opening of the rotary disk. The bed table 3 for placing the object 6 is carried in the opening. The rotary disk is circularly driven around the object 6 by driving force transmitted through the drive transmission system from the rotary disk driving device to be controlled by the gantry controller 208 of the scanning controller 20.

The X-ray source 201 is comprised of an X-ray tube and a high-voltage generation device. The X-ray source 201 is controlled by the X-ray controller 202 of the scanning controller 20 and irradiates a predetermined intensity of X-ray continuously or intermittently. The X-ray controller 202 of the scanning controller 20 controls an X-ray tube voltage and an X-ray tube current to be applied or supplied to the X-ray tube according to the X-ray tube voltage and the X-ray tube current determined by the image processing device 40. The X-ray source 201 is provided with a collimator and irradiates an X-ray emitted from the X-ray source 201 to the object 6 as an X-ray such as a cone beam (whose shape is cone or pyramid). An opening width of the collimator is controlled by the scanning controller 20. An X-ray transmitted through the object 6 enters the X-ray detector 205.

In the X-ray detector 205, an X-ray detection element group is comprised of the combination of, for example, a scintillator and a photodiode, approximately 1,000 X-ray detection element groups are arranged in the channel direction (circular direction), approximately 1 to 320 X-ray detection element groups are arranged in the column direction (body-axis direction) for example, and those groups are arranged opposite to the X-ray source 201 across the object 6. The X-ray detector 205 detects an amount of X-ray irradiated from the X-ray source 201 and transmitted through the object 6 and outputs the amount to data acquisition system (DAS) 206. The DAS 206 acquires an X-ray amount to be detected by the individual X-ray detection elements of the X-ray detector 205, converts into digital data, and outputs it to the reconstruction calculator 43 in order as transmission X-ray data.

The scanning controller 20 comprises the X-ray controller 202 for controlling X-ray irradiation, the gantry controller 208 for controlling rotational operation of the gantry 2, the table controller 207 for controlling moving operation, and the DAS (Data acquisition system) 206 for performing acquisition operation of projection data.

The bed table 3 adjusts its height properly according to a control signal to be sent from the table controller 207 of the scanning controller 20 and also moves back and forth in the body-axis direction as well as moves in a direction vertical to the body axis and parallel to the top plate (left and right direction). Hence, the object 6 is carried in and out of the opening (the X-ray irradiation space) of the gantry 2.

Figure 2:
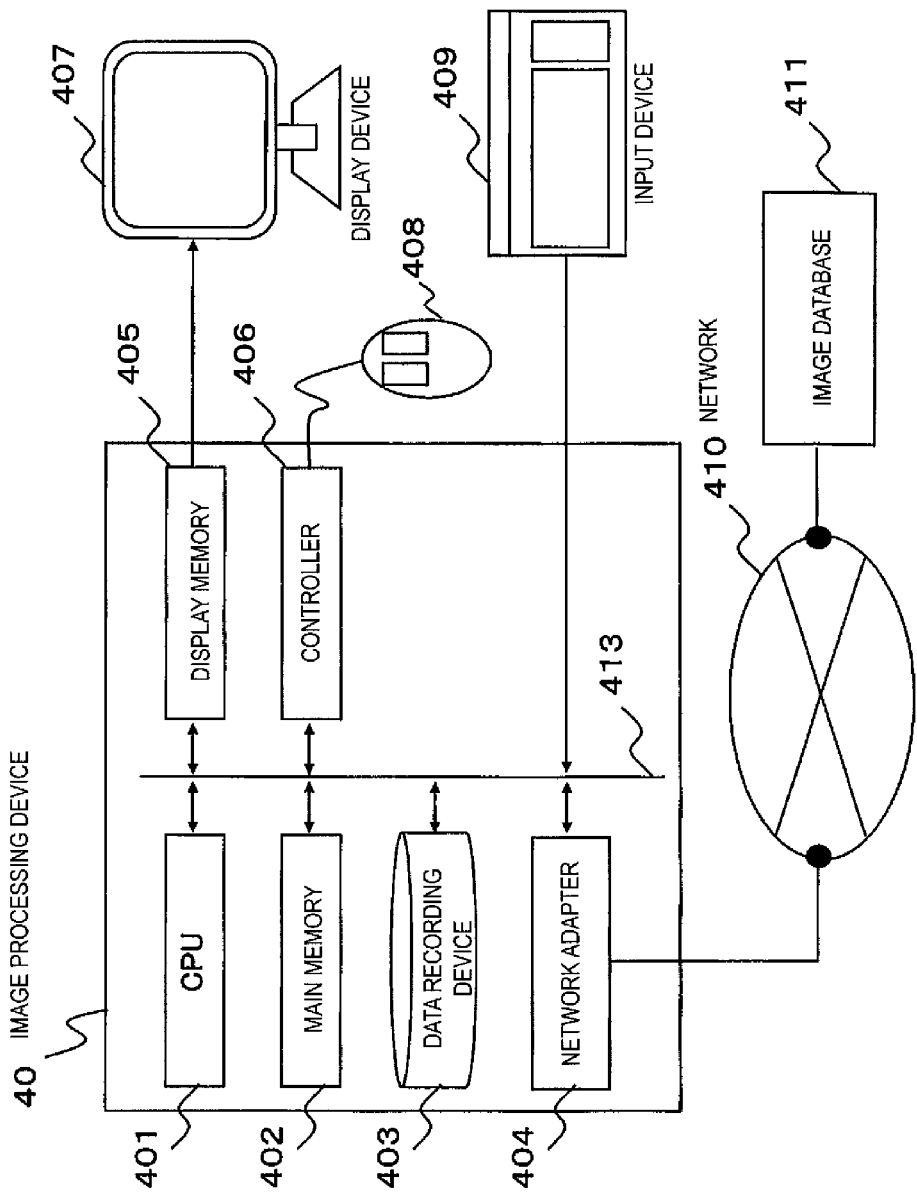
FIG. 2 is a hardware configuration diagram of the image processing device 40 used for the X-ray CT apparatus 1.

The image processing device 40 is a computer comprising the CPU (Central Processing Unit) 401, the main memory 402 such as a ROM (Read Only Memory) and a RAM (Random Access Memory), the data recording device 403 such as a hard disk, the network adapter 404, the display memory 405, the controller 406, the display device 407, the input device 409, and the like as shown in FIG. 2. Programs, data, and the like to achieve the functions of the X-ray CT apparatus 1 are stored in a storage unit of the image processing device 40 (the main memory 402 or the data recording device 403) in advance.

The image processing device 40 transmits a control signal according to the scanning conditions set by an operator to the scanning controller 20. The scanning controller 20 irradiates an X-ray to the object 6 while controlling a rotational speed of the gantry 2, an amount of X-ray to be irradiated from the X-ray source 201, and a position of the bed table 3 based on a control signal input from the image processing device 40. Also, the image processing device 40 acquires transmission X-ray data detected by the X-ray detector 205 and acquired by the DAS 206 and send it to the reconstruction calculator 43.

The reconstruction calculator 43 acquires the transmission X-ray data input from the DAS 206 and performs pre-processing such as logarithmic transformation and sensitivity correction to generate a projection data set required for reconstruction. Also, the reconstruction calculator 43 reconstructs an image such as a tomographic image using the generated projection data set. The image data reconstructed by the reconstruction calculator 43 is input to the image processing device 40 and stored in the data recording device 403.

The display device 407 is comprised of a display device such as a liquid crystal panel and a CRT monitor and a logic circuit to execute a display process in conjunction with a display device and connected to the image processing device 40. The display device 407 displays a reconstructed image output from the reconstruction calculator 43 as well as various types of information used by the image processing device 40.

The input device 409 is comprised of pointing devices such as a keyboard and the mouse 408, a numerical keypad, various switch buttons, etc. and outputs various types of commands and information to be input by an operator to the image processing device 40. The operator operates the X-ray CT apparatus 1 interactively using the display device 407 and the input device 409. The input device 409 may be used as a touch panel type input device that is integrally configured with the display window of the display device 407.

Figure 3:
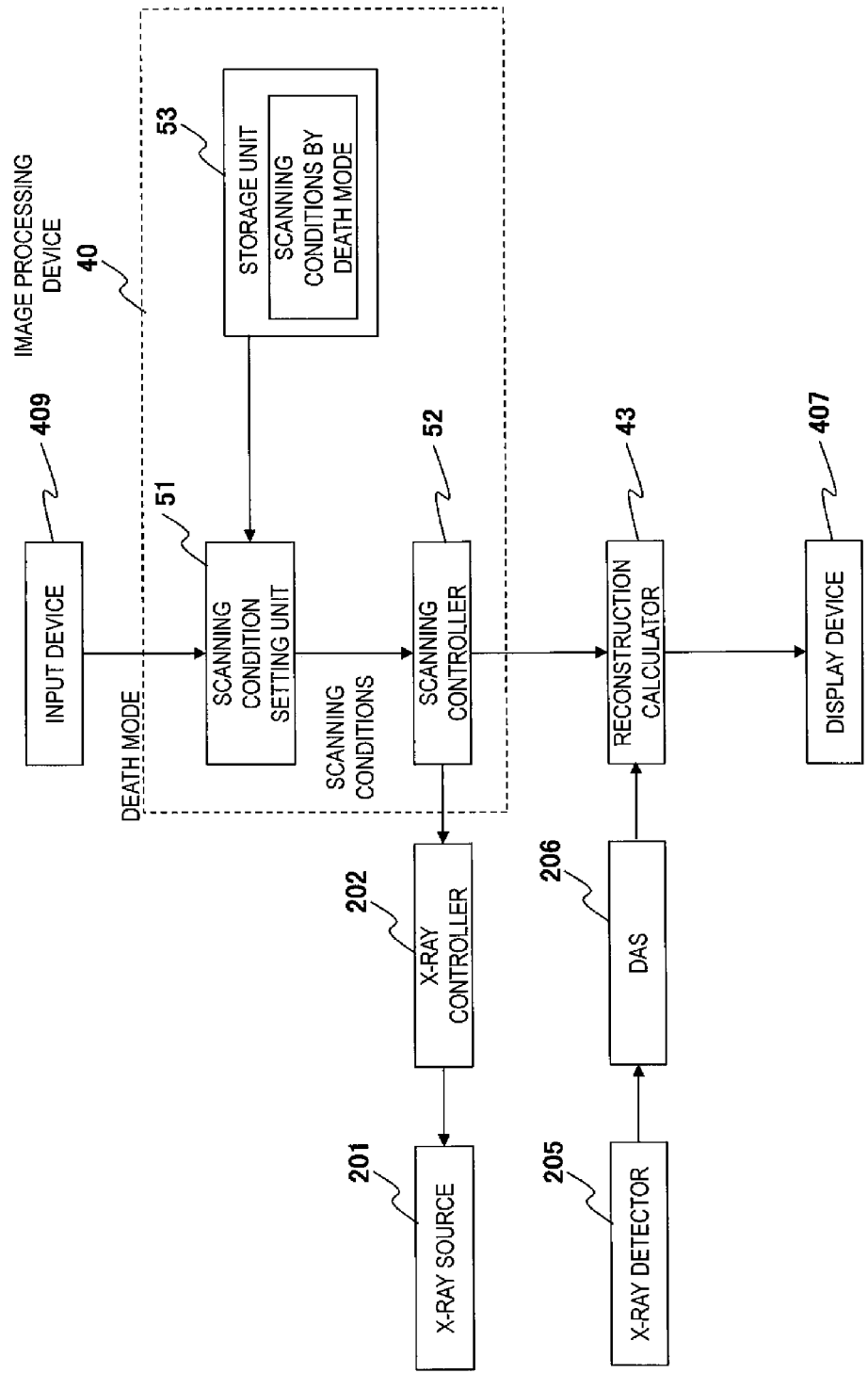
FIG. 3 is a diagram showing the basic functional configuration of the image processing device 40.

Next, referring to FIG. 3, the functional configuration of the X-ray CT apparatus 1 will be described.

The image processing device 40 related to the present invention has the scanning condition setting unit 51, the scanning controller 52, and the storage unit 53 as the basic configuration.

The scanning condition setting unit 51 reads scanning conditions according to the death mode input from the input device 409 out of the storage unit 53 and transmits them to the scanning controller 52.

The storage unit 53 keeps a plurality of the scanning conditions according to the death mode. The death mode includes death by fire, death by drowning, head injury, thoracoabdominal injury, head disease, heart disease, and the other various modes as options for example. The scanning conditions are various parameters such as a scanning site, a tube voltage, a tube current, a slice thickness, and a pitch. It is desirable that at least two types of scanning conditions: recommended conditions for standard scanning and high-resolution scanning are set for each death mode.

FIG. 4 is an example of the scanning conditions by death mode 8. In the scanning conditions by death mode 8 shown in FIG. 4, the items to be set are a site for which standard scanning is performed in each mode and the recommended conditions for standard scanning as well as a site for which high-resolution scanning is performed and the recommended conditions for high-resolution scanning in each mode.

The mode is an option of a death mode and includes, for example, "1. CHARRED BODY", "2. DROWNED BODY", "3. HEAD INJURY", "4. THORACOABDOMINAL INJURY", "5. HEAD DISEASE", "6. HEART DISEASE", and "7. OTHERS". "7. OTHERS" is a mode to be selected in a case where the cause of death is unknown because no injury was found or the like.

Standard scanning is performed for the whole body in each mode, as well as high-resolution scanning is performed for a certain site in each mode.

For example, when the mode is set to "1. CHARRED BODY", a site for which high-resolution scanning is to be performed is set to "PELVIS PORTION". Then, the recommended conditions for standard scanning are set to the tube voltage: 120 [kV], the tube current: 100 [mA], the slice width: 1.2 [mm], and the pitch: 1.2. Also, the recommended conditions for high-resolution scanning are set to the tube voltage: 120 [kV], the tube current: 200 to 300 [mA], and the slice width: 0.625 [mm].

When the mode is "2. DROWNED BODY", a site for which high-resolution scanning is to be performed is set to "LUNG FIELD". When the mode is "3. HEAD INJURY", a site for which high-resolution scanning is to be performed is set to "HEAD PORTION", and when the mode is "4. THORACOABDOMINAL INJURY", a site for which high-resolution scanning is to be performed is set to "THORACOABDOMINAL PORTION". When the mode is "5. HEAD DISEASE", a site for which high-resolution scanning is to be performed is set to "HEAD PORTION". When the mode is "6. HEART DISEASE", a site for which high-resolution scanning is to be performed is set to "HEART". When the mode is "7. OTHERS", "WHOLE BODY" is set as a site for which standard scanning is to be performed.

Additionally, the values of each parameter and the sites set as the scanning conditions are recommended values, and it may be configured so that they can be changed to arbitrary values by an operator. Also, a site for which high-resolution scanning is to be performed is not limited to one site, but the high-resolution scanning may be performed for two or more sites.

Additionally, the storage unit 53 may store various scanning conditions for scanning a living body in addition to those for a corpse. It is suitable for when scanning a corpse using a medical X-ray CT apparatus.

The scanning controller 52 performs scanning while controlling an X-ray amount, a gantry rotation speed, a bed speed, and the like according to the scanning conditions set by the scanning condition setting unit 51. Also, the scanning controller 52 transmits image reconstruction conditions according to the death mode to the reconstruction calculator 43.

The reconstruction calculator 43 reconstructs a tomographic image and a diagnostic image according to the reconstruction conditions set by the scanning controller 52 based on transmission X-ray data acquired by scanning. The diagnostic image is, for example, an MRP (Multi Planer Reconstruction) image generated based on three-dimensional volume data comprised of acquired tomographic images, an MIP (Maximum Intensity Projection) image, a VR (Volume Rendering) image, or the like. It is desirable that a site and a type of image to be reconstructed are determined in advance according to the death mode.

For example, the respective reconstruction conditions (a reconstruction thickness, a reconstruction FOV, a filter function, and the like) are set for each mode of the scanning conditions by death mode 8. Also, it may be configured so that a type (Sagittal, MPR, MIP, or the like) of a diagnostic image to be generated based on a reconstructed tomographic image and a parameter required for generating each diagnostic image are set in advance. In this case, the diagnosis can be performed efficiently because an image required for the diagnosis is generated continuously after scanning.

Next, the operations of the X-ray CT apparatus 1 will be described. First, referring to FIG. 5, the overall flow of the scanning process will be described.

The CPU 401 of the image processing device 40 of the X-ray CT apparatus 1 related to the present invention reads programs and data for the scanning process shown in FIG. 5 from the main memory 402 and executes the process based on the programs and data.

The image processing device 40 of the X-ray CT apparatus 1 displays the death mode selection window 7 on the display device 407 before scanning (Step S101). An example of the death mode selection window 7 is shown in FIG. 6.

The death mode selection window 7 displays the whole body image 71 and the buttons 72 to 78 that are the options of each death mode. The button 72 is the charred body mode, the button 73 is the drowned body mode, the button 74 is the head injury mode, the button 75 is the thoracoabdominal injury mode, the button 76 is the head disease mode, the button 77 is the heart disease mode, and the button 78 is the others mode.

The whole body image 71 may be used as a positioning image to be scanned in advance before the main scanning and as an illustration. For example, when a mouse pointer is moved to any of the buttons 72 to 78, it may be configured so that a mark is displayed on a site for which high-resolution scanning is to be performed in a mode corresponding to the button indicated by the mouse pointer and a display mode is changed.

When a mouse-click operation and touch operation is performed on any of the buttons 72 to 78 of the death mode selection window 7, a death mode is input in the CPU 401 of the image processing device (Step S102). The CPU 401 acquires scanning conditions according to the input death mode from the storage unit 53 (Step S103). For example, when the "1. CHARRED BODY" button 72 in FIG. 6 is selected, the scanning conditions of the charred body mode are read out of the scanning conditions by death mode 8 stored in the storage unit 43. The CPU 401 sets the read-out scanning conditions and performs scanning based on the scanning conditions (Step S104).

During scanning, the scanning controller 202 generates an X-ray control signal, a gantry control signal, and a bed table control signal based on scanning conditions to be input from the image processing device 40 to transmit them to each controller. The scanning controller 202 supplies an electric power signal and an X-ray generation timing signal to the X-ray source 201. The gantry controller 208 controls a rotational speed and a position of the components on the gantry 2 according to the scanning conditions. Also, the table controller 207 moves the bed table 3 to a position determined by the image processing device 40 according to the scanning conditions and also controls the bed table 3 so as to be a predetermined moving speed. An X-ray entering the X-ray detector 205 transmitted through the object 6 is converted into a digital signal by the DAS 206, and it is transmitted as transmission X-ray data to the image processing device 40. The image processing device 40 transmits the acquired transmission X-ray data to the reconstruction calculator 43.

The reconstruction calculator 43 performs predetermined pre-processing such as a correction process for the transmission X-ray data acquired from the image processing device 40 and generates a projection data set to reconstruct an image (Step S105). The reconstructed image is stored in the data recording device 403 of the image processing device 40 as well as is displayed on the display device 407 (Step S106).

In the following respective embodiments, processes in representative modes will be described respectively.

First Embodiment

Referring to FIGS. 7 to 11, the first embodiment of the present invention will be described.

In the first embodiment, "1. CHARRED BODY" will be described from among the respective modes of the above death modes.

A sex of a living human body can be determined by the statement of the person or the physical characteristics. However, it may be difficult to determine a sex of an unidentified corpse and a charred body particularly. In particular, it is extremely difficult to determine a sex of a charred body whose whole body has been damaged by carbonization.

In order to solve such a problem, the X-ray CT apparatus 1 of the first embodiment automatically sets scanning conditions appropriate for a charred body when the charred body mode is selected as well as estimates a sex by image diagnosis continuously after scanning to output the sex estimation result.

Figure 7:
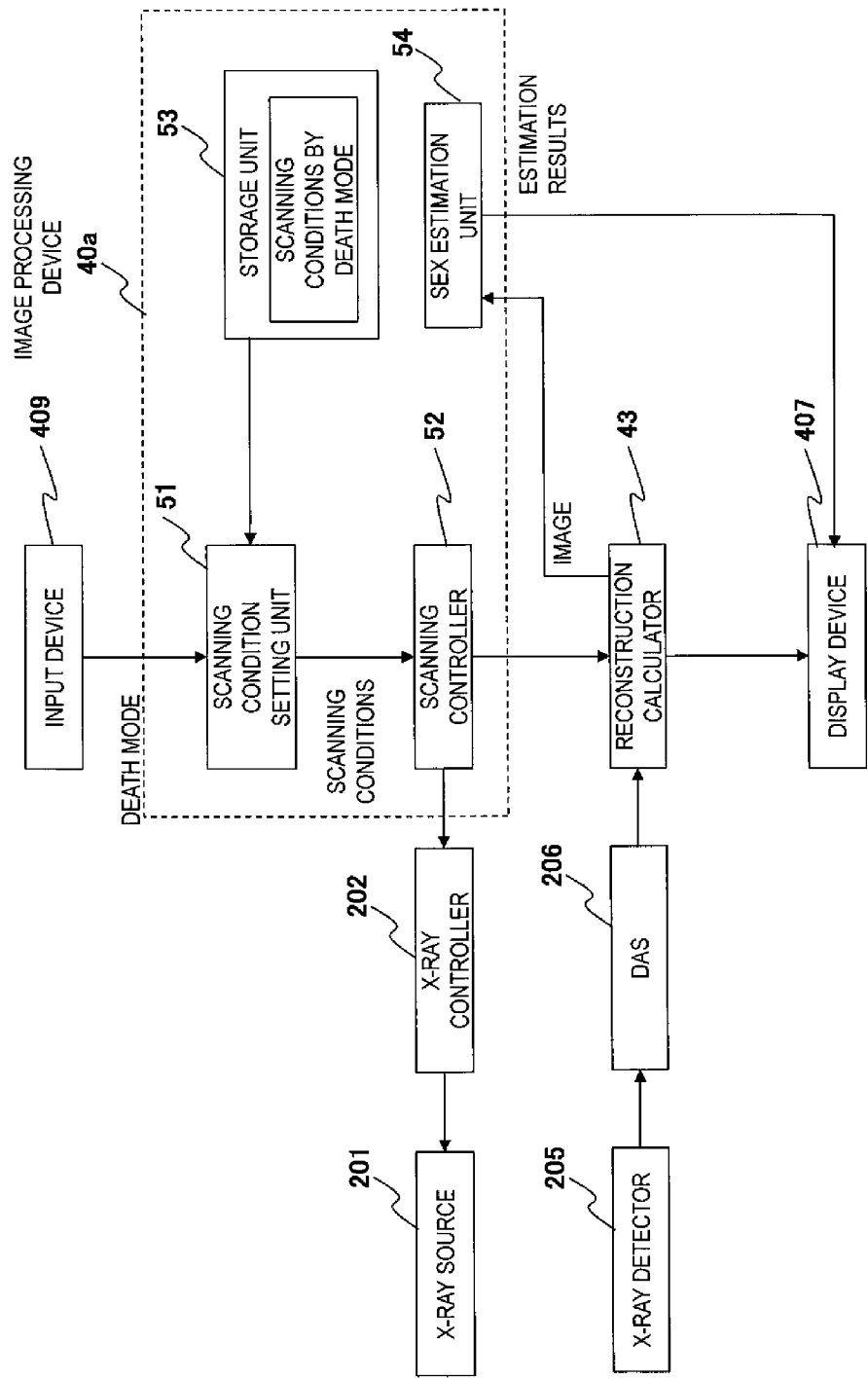
FIG. 7 is a diagram showing the functional configuration of the image processing device 40a of the first embodiment.

FIG. 7 is a diagram showing the functional configuration of the image processing device 40a of the first embodiment. The image processing device 40a further includes the sex estimation unit 54 in addition to the basic configuration of the image processing device 40 of FIG. 3.

The sex estimation unit 54 calculates a lower angle α of the pubic bone based on an image of the pelvis portion generated by the reconstruction calculator 43. Then, based on the lower angle α of the pubic bone, the results such as "Male", "Female", and "Unable to Estimate" are generated. The sex estimation result is stored in linkage with the corpse image and the examination information in the storage unit 53. Also, the sex estimation result is displayed on the display device 407. It is desirable that the diagnostic image to be used for the sex estimation is, for example, a front image of the corpse or an MPR image whose cutting surface is along the inclination of the pelvis. In the MPR image, for example, it is desirable that a surface including the three points of the lower end 91 of the pubis and the lower ends 92 and 93 of the ischia on both sides (refer to FIG. 11) is set in order to set this surface as a cutting surface of the MPR image. A lower angle α of the pubic bone can be calculated based on a density value change between the born portion and the air in the diagnostic image.

Figure 8:
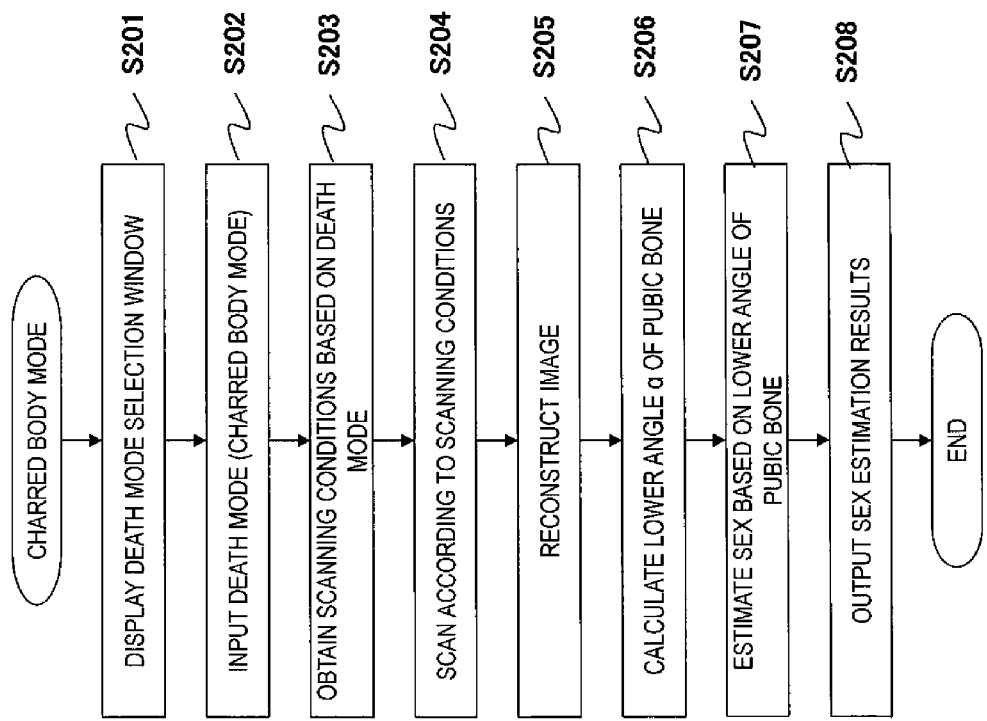
FIG. 8 is a flow chart explaining the flow of the scanning process in the charred body mode to be executed by the X-ray CT apparatus 1 of the first embodiment.

Referring to the flow chart in FIG. 8, the flow of the sex estimation process of the first embodiment will be described.

Additionally, because the hardware configurations of the X-ray CT apparatus 1 of the first embodiment and the image processing device 40 are similar to FIGS. 1 to 2, the repeated descriptions are omitted, and hereinafter, the same symbols are provided for the configuration parts same as each part shown in FIGS. 1 and 2.

As shown in FIG. 6, the CPU 401 (the scanning condition setting unit 51) of the image processing device 40 first displays the death mode selection window 7 on the display device 407 (Step S201). When the selection command "1. CHARRED BODY" mode is input from the input device 409 (Step S202), the CPU 401 acquires the scanning conditions of the "1. CHARRED BODY" mode from the storage unit 53 (the main memory 402 or the data recording device 403) (Step S203). The acquired scanning conditions are input to the scanning controller 52.

Figure 9:
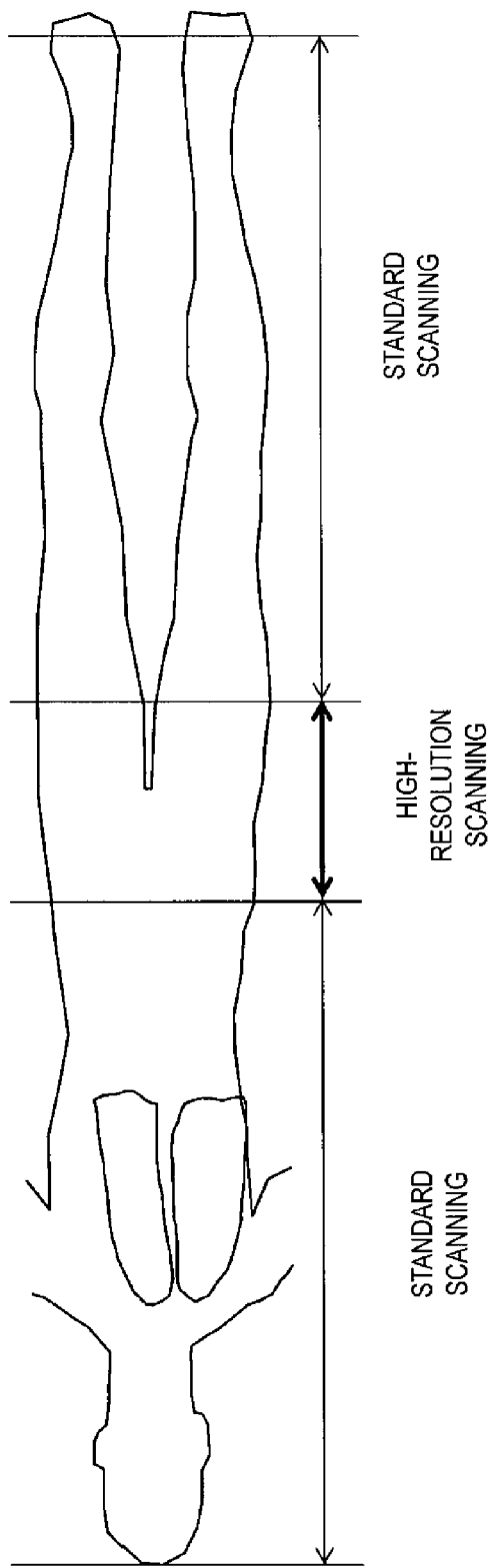
FIG. 9 is a diagram explaining the two-stage scanning in the charred body mode.

In case of the "1. CHARRED BODY" mode, high-resolution scanning is performed for the pelvis portion as shown in FIG. 9, and the scanning conditions to perform standard scanning for the whole body other than the pelvis portion are set in order to estimate a sex of the corpse based on a shape of the pelvis portion, the high-resolution scanning is performed for the pelvis portion.

The specific scanning conditions are set so that a site for standard scanning is "whole body" and a site for high-resolution scanning is "pelvis portion (or the spinal column)", and the recommended conditions for the standard scanning are set to the tube voltage: 120 [kV], the tube current: 100 [mA], the slice width: 1.2 [mm], the pitch: 1.2, etc. Also, the recommended conditions for the high-resolution scanning are set to the tube voltage: 120 [kV], the tube current: 300 [mA], the slice width: 0.625 [mm], etc.

The scanning controller 52 performs scanning while controlling an X-ray amount, a gantry rotation speed, a bed speed, and the like according to the scanning conditions set by the scanning condition setting unit 51 (Step S204).

For example, standard scanning is performed from the head portion to the start position of the pelvis portion by the spiral scan, and the scan is changed to high-resolution scanning when the scan arrives at the start position of the pelvis portion. The axial scan is performed for the pelvis portion. The scan goes back to the standard scanning by the spiral scan again when the scan passed by the end position of the pelvis portion, and the standard scanning is performed to the toe tip. The position of the pelvis portion can be located by positioning scanning to be performed before scanning.

The reconstruction calculator 43 reconstructs a tomographic image and diagnostic image according to the reconstruction conditions set by the scanning controller 52 (Step S205). The pelvis portion is reconstructed using a high-resolution CT image. Also, a portion other than the pelvis portion is reconstructed using a CT image with standard image quality. The reconstruction calculator 43 generates a diagnostic image suitable for sex estimation and outputs it to the sex estimation unit 54.

The CPU 401 (the sex estimation unit 54) of the image processing device 40 estimates a sex based on an image of the pelvis portion generated by the reconstruction calculator 43 (Steps S206 to S207).

Even in cases of a charred body, a bone in a deeper part is seldom burned completely in the most cases. Therefore, a sex can be estimated, for example, from the shape of the pelvis in many cases.

FIG. 10 is a schematic diagram showing the shapes of the pelvis portions of a male in (a) and a female in (b). As shown in FIG. 10, it is characterized that the female pelvis is totally larger than the male pelvis. However, a sex difference between a male and female cannot be physically estimated only by the feature that the female pelvis is simply larger. Therefore, the sex estimation unit 54 of the first embodiment sets a lower angle α of the pubic bone formed by meeting both the pubic arches just below the pubic symphysis as a designated standard. It is generally said that a lower angle α of the pubic bone of a male is narrower that of a female. More specifically, the average angle of a male is 60 degrees, and that of a female is 80 degrees.

Therefore, for example, a sex is defined as a male when a lower angle α of the pubic bone is less than 65 degrees and defined as a female when a lower angle α of the pubic bone is 75 degrees or more. Also, in a case where a lower angle α of the pubic bone is 65 degrees or more and less than 75 degrees, the sex is defined as impossible estimation. Additionally, the defining numerical values are examples, and they can be changed to the other numerical values. For example, it is desirable that appropriate numerical values are defined by considering regional characteristics, races, and the like. It may be configured so that a numerical value input window is displayed on the display device 407 and an operator can input from the input device 409 in order to change a numerical value to be a criterion.

As a diagnostic image to be used for measuring a lower angle α of the pubic bone, for example, a two-dimensional image (front image) in which a 3D image of the pelvis portion is projected from the front and an MPR image are suitable.

Figure 11:
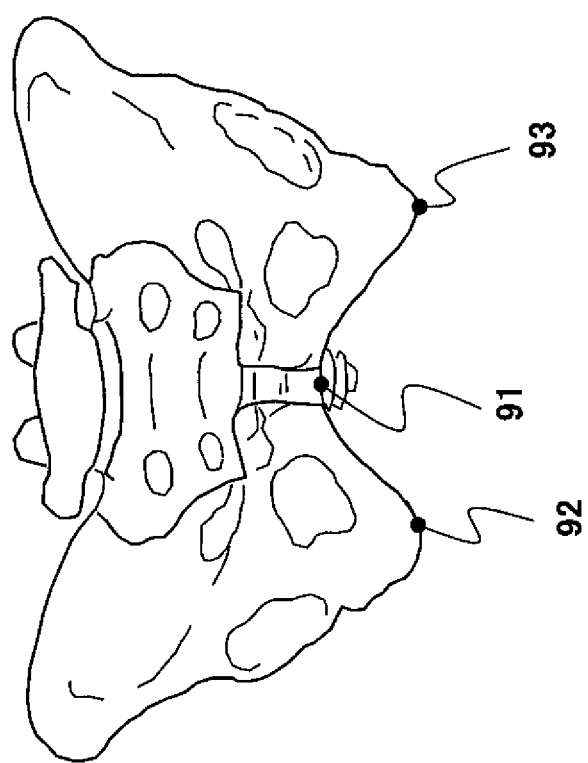
FIG. 11 is a diagram showing the respective points to determine a cutting surface when generating an MPR image of the pelvis portion.

In case of an MPR image, as shown in FIG. 11, for example, it is desirable to generate an MPR image by setting a surface including the three points of the lower end 91 of the pubis and the lower ends 92 and 93 of the ischia on both sides as a cutting surface.

The image processing device 40 (the sex estimation unit 54) calculates a lower angle α of the pubic bone based on a front image of the pelvis portion generated by the reconstruction calculator 43 or a density value change between the born portion and the air in an MPR image (Step S206). Then, according to the above definition, for example, a sex is consequently determined as a male when "α" is less than 65 degrees, as a female when "α" is 75 degrees or more, and as impossible estimation when "α" is 65 degrees or more and less than 75 degrees (Step S207). The sex estimation result is stored in linkage with the corpse image and the examination information in the storage unit 53 and is also displayed on the display device 407 (Step S208).

As described above, in the charred body mode, the scanning conditions to perform high-resolution scanning for the pelvis portion and standard scanning for the other sites are set in advance. Also, the included is the function to estimate a sex using an image of the pelvis portion. Hence, the procedure from scanning to reconstructing an appropriate image can be performed smoothly by a simple operation of selecting a death mode. For example, in a case where a number of corpses are carried concentratively due to a large-scale fire etc., efficient X-ray CT scanning can be performed by setting scanning conditions with a simple operation. Also, after the scanning, a high-resolution image of the pelvis portion is reconstructed to estimate a sex. This can be helpful for revealing an identity of a corpse whose sex cannot be determined.

Also, because the whole body is scanned, each part other than the pelvis portion can be examined. For example, if unnatural damage and the like are found in the skull bones of a charred body, the cause of death other than by fire such as beating the head portion can be possibly found.

Second Embodiment

Figure 12:
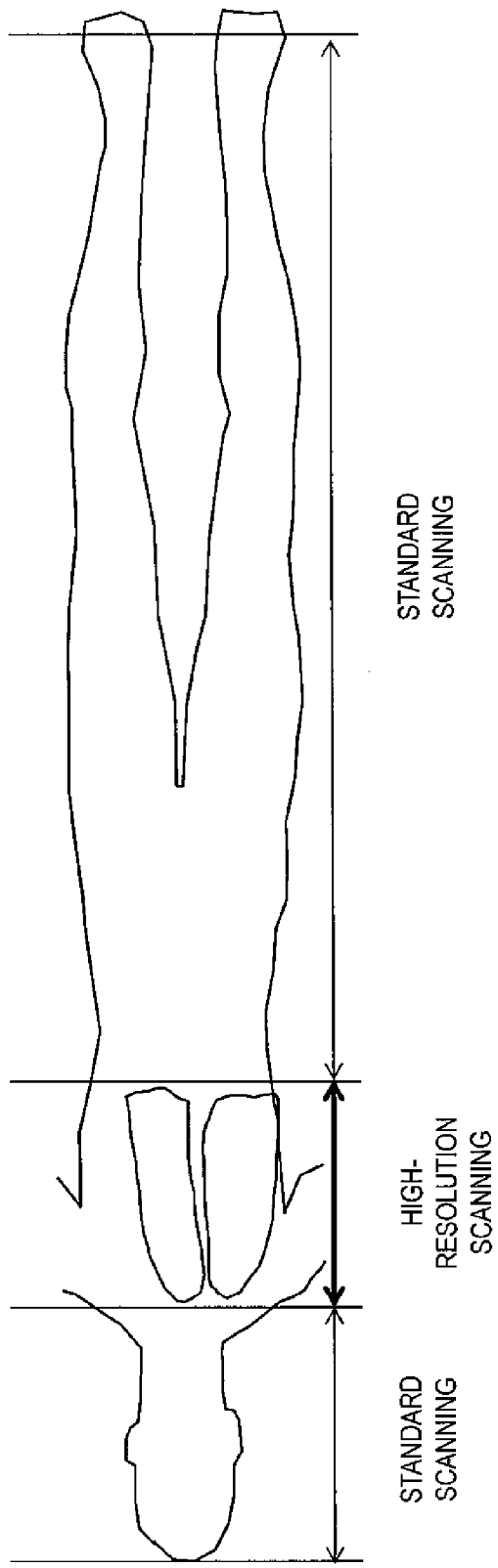
FIG. 12 is a diagram explaining the two-stage scanning in the drowned body mode.
Figure 13:
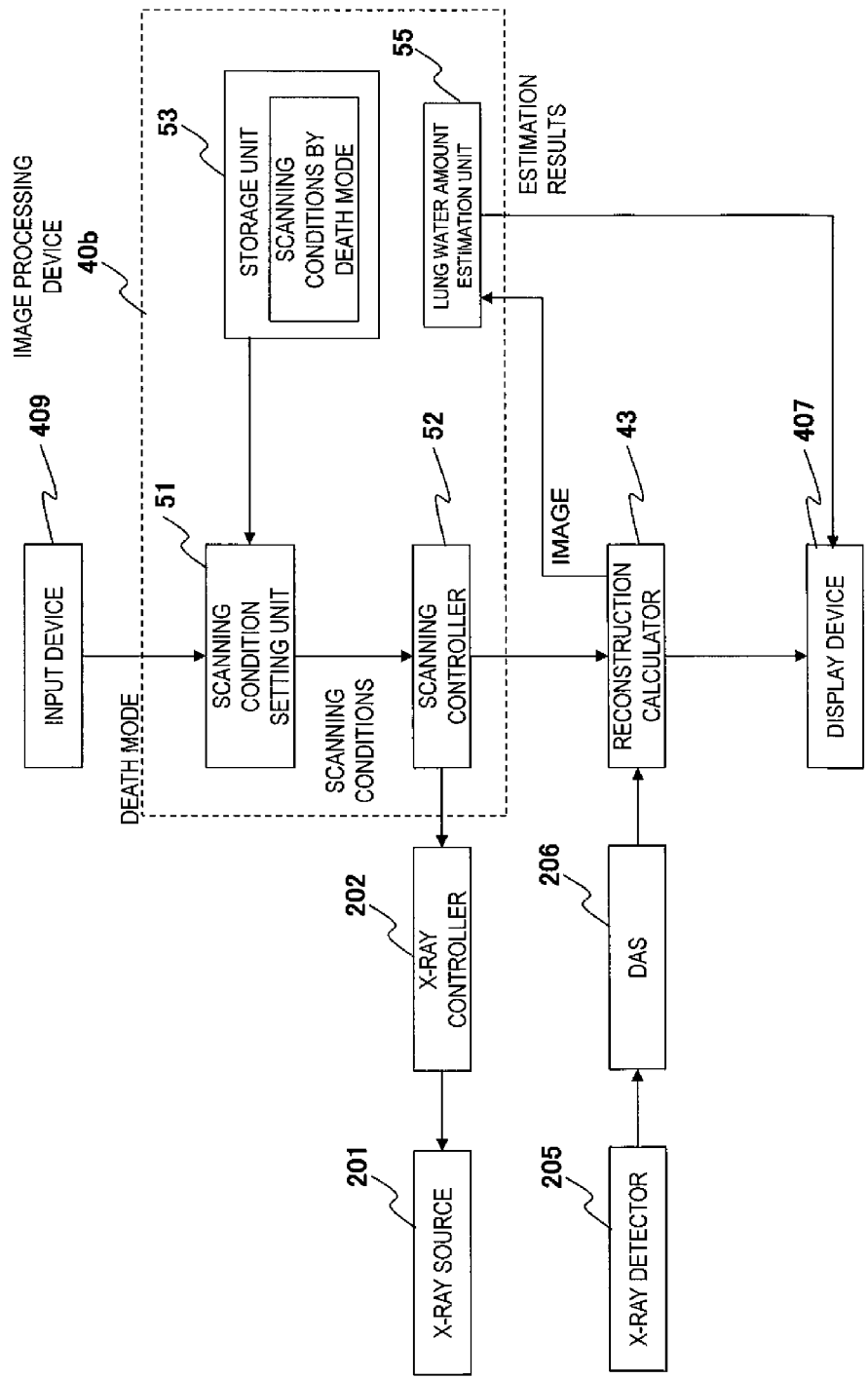
FIG. 13 is a diagram showing the functional configuration of the image processing device 40b of the second embodiment.

Referring to FIGS. 12 to 13, the second embodiment of the present invention will be described.

In the second embodiment, the "2. DROWNED BODY" mode will be described from among the above respective death modes.

In the drowned body mode, similarly to the charred body mode, the two-stage scanning of whole-body scanning by standard scanning and high-resolution scanning is performed. As shown in FIG. 12, the drowned body mode is different from the charred body mode in a point where a position of high-resolution scanning is set to the lung field.

Also, in the drowned body mode, the lung water amount estimation unit 55 that estimates by image diagnostic a water amount of the lung field is further included.

FIG. 13 is a diagram showing the functional configuration of the image processing device 40b of the second embodiment. The image processing device 40b further includes the lung water amount estimation unit 55 in addition to the basic functional configuration of the image processing device 40 of the present invention shown in FIG. 3.

The lung water amount estimation unit 55 calculates a water amount in the lung based on a lung field image generated by the reconstruction calculator 43. The results are stored in linkage with the corpse image and the examination information in the storage unit 53. Also, the water amount in the lung is displayed on the display device 407. In order to estimate the water amount in the lung, for example, a plurality of two-dimensional CT images (tomographic images) are acquired to convert into a three-dimensional image, and then the number of voxels having CT values equivalent to water is counted. Also, a three-dimensional image may be generated to extract regions having CT values equivalent to water by threshold value and the like.

As described above, the two-stage scanning conditions, in which high-resolution scanning is performed for the lung field and standard scanning is performed for the other sites, are previously set in the drowned body mode. Also, the mode has a function to estimate a water amount in the lung using the lung field image. When the lung field is dissected in an anatomical operation, the inside water flows out, and information about how much water was taken in cannot be obtained. However, by using the X-ray CT apparatus 1 of the second embodiment, the water amount in the lung can be estimated without the dissection, which can figure out an accurate water amount at the time of death. For example, it is possible to find a possibility of the cause of death other than by drowning in a case where the water amount in the lung is small in spite of a drowned body, and the like. Even in such a case, because the whole body was already scanned, there is no need to perform X-ray CT scanning again, which can investigate the possibility of the other causes of death. Also, in case of a large-scale flood disaster, a number of corpses can be scanned efficiently to check the states of the corpses.

Third Embodiment

Figure 14:
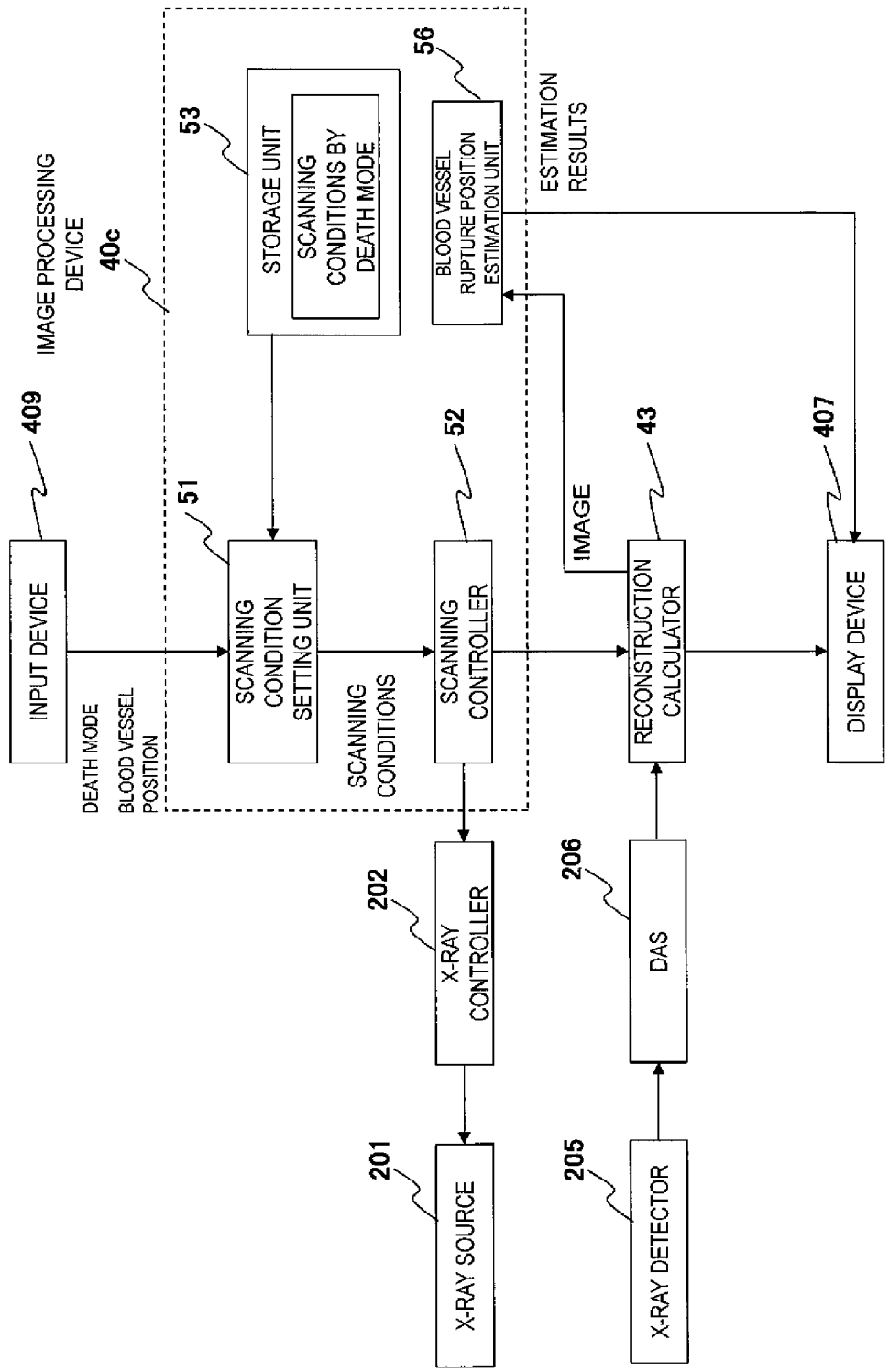
FIG. 14 is a diagram showing the functional configuration of the image processing device 40c of the third embodiment.

Referring to FIGS. 14 to 16, the third embodiment of the present invention will be described.

In the third embodiment, a process to estimate a ruptured position in a blood vessel is executed based on an image generated by the reconstruction calculator 43. A blood vessel rupture position may be estimated in any of the above respective modes. Also, the process can be applied to blood vessels on any sites. For example, estimating a blood vessel rupture position for blood vessels in the head portion in the "5. HEAD DISEASE" mode can be utilized to determine whether or not there is a cerebral hemorrhage.

The functional configuration of the image processing device 40c including the blood vessel rupture position estimation unit 56 is shown in FIG. 14. The image processing device 40c of the third embodiment further includes the blood vessel rupture position estimation unit 56 in addition to the basic functional configuration of the image processing device 40 of the present invention shown in FIG. 3.

The blood vessel rupture position estimation unit 56 estimates a rupture position of a blood vessel from an image generated by the reconstruction calculator 43. The target image may be a three-dimensional image in which tomographic images are acquired, an MIP image in which bone regions were removed, an MPR image along the blood vessel, or the like. The blood vessel rupture position estimation unit 56 extracts a blood vessel region by the region growing method for example, and then identifies a position where blood leaks out. The region growing process compares density values (CT values) of adjacent pixels in order from the start point, extracts pixels when the pixel values are close, does not extract pixels (whose density values are not within a predetermined range) when the pixel values are different, and then grows the extraction region in order.

FIG. 15 is a schematic diagram showing the blood vessel 90. As shown in FIG. 15(*a*), when the above region growing process is performed for an arbitrary point inside the blood vessel 90 by setting the start point 94 set by an operator as a base point an operator, a region (hereinafter, referred to as the leakage region 96) where blood leaked out as shown in FIG. 15(*b*) is also extracted, and then the region grows. Because a blood concentration in the leakage region 96 is lower than blood in the blood vessel, the concentration difference appears in the CT value. By setting the CT value difference as an index, the blood vessel rupture position estimation unit 56 determines whether or not each pixel in the extracted blood region is in the blood vessel or in the leakage region 96.

In the blood region extracted by the region growing method, a point where a CT value changes extremely can be estimated as the rupture position 95. The blood vessel rupture position estimation unit 56 provides a mark for the rupture position 95 in the blood vessel on an image before storing the image and displays the image to which the mark was provided on the display device 407.

FIG. 16 is a flow chart explaining the flow of the blood vessel rupture position estimation process. The blood vessel rupture position estimation process is executed after scanning in any one mode completes.

The CPU 401 of the image processing device 40c of the X-ray CT apparatus 1 related to the present invention reads programs and data for the scanning process shown in FIG. 16 from the main memory 402 and executes the process based on the programs and data.

After the scanning completes, the CPU 401 of the image processing device 40c first receives an input of a blood vessel position from the input device 409 (Step S301). In order to specify the blood vessel position, for example, a mouse or the like specifies an arbitrary position in a positioning image displayed on the display device 407. Also, any of the scanning modes may be available.

Next, the CPU 401 reconstructs a blood vessel image in a position specified in Step S301 (Step S302). The blood vessel image is a suitable image for diagnosing a blood vessel (blood). For example, the image is a 3D image, MPR image, MIP image after bones were removed, or the like. The CPU 401 displays the reconstructed blood vessel image on the display device 407.

Next, the CPU 401 of the image processing device 40c receives a setting for the start point 94 of the region growing process (Step S303). The start point 94 is set by specifying an arbitrary position inside a blood vessel in a blood vessel image generated in Step S302 with a mouse or the like.

The CPU 401 of the image processing device 40c executes the region growing process by setting the start point 94 set in Step S302 as a starting point (Step S304). Then, the rupture position 95 in a blood vessel is estimated from the region growing results (Step S305). As described above, the rupture position 95 in a blood vessel can be estimated, for example, based on a difference between a pixel value inside the blood vessel and that in the leakage region 96.

After the rupture position 95 is estimated, a mark is provided in the estimated position on the blood vessel image and displayed on the display device 407 (Step S306).

As described above, a blood vessel rupture position of a corpse can be estimated in the present embodiment. Therefore, a cause of death or a state at the time of death can be efficiently investigated or understood.

Additionally, the blood vessel rupture position estimation process may be set so as to be performed continuously after scanning or may be set so as to be performed by reading an image generated in advance and stored in the storage unit 53.

Although the X-ray CT apparatus related to the present invention and suitable embodiments for the scanning condition setting method are described above, the present invention is not limited to the above embodiments. Although the seven types of the death modes including death by fire, death by drowning, head injury, thoracoabdominal injury, head disease, heart disease, and the others are exemplified in the above embodiments for example, a mode other than these modes may be included. Also, scanning conditions recommended in each mode, sites for high-resolution scanning, and the like are an example, and the other numerical values and sites may be used. Also, two or more sites for which high-resolution scanning is performed may be used as needed.

Additionally, it is apparent that a person skilled in the art could arrive at various modified examples or amended examples within the scope of the technical ideas disclosed in the present invention, and it is understood that these naturally belong to the technical scope of the present invention.

DESCRIPTION OF REFERENCE NUMERALS

1: X-ray CT apparatus
2: gantry
20: scanning controller
201: X-ray source
202: X-ray controller
205: X-ray detector
206: DAS
3: bed table
40: image processing device
401: CPU
402: main memory
407: display device
43: reconstruction calculator
51: scanning condition setting unit
52: scanning controller
53: storage unit
54: sex estimation unit
55: lung water amount estimation unit
56: blood vessel rupture position estimation unit
7: death mode selection window
8: scanning conditions by death mode

The invention claimed is:

1. An X-ray CT apparatus comprising:
an X-ray source that generates an X-ray;
an X-ray detector that detects an X-ray transmitted through an object;
a data acquisition system that acquires data of the transmitted X-ray detected by the X-ray detector;
a storage unit that stores scanning conditions according to a death mode;
an input unit that allows an operator to select the death mode;
a scanning controller that reads scanning conditions according to the selected death mode from the storage unit and scanning according to the read scanning conditions; and
a reconstruction calculator that reconstructs an image according to the death mode using the transmission X-ray data acquired from the data acquisition system during scanning;
wherein death by fire, death by drowning, head injury, thoracoabdominal injury, head disease, heart disease, and the others are included as input mode options of the death mode, and
a site for high-resolution scanning and recommended scanning conditions for the said site according to each death mode are included in the scanning conditions in addition to recommended scanning conditions for performing standard scanning for the whole body.

2. The X-ray CT apparatus according to claim 1,
wherein a site for which high-resolution scanning is performed is the pelvis portion in a case where the death mode is death by fire, and
the reconstruction calculator reconstructs at least a high-resolution image of the pelvis portion and further includes a sex estimation unit that estimates a sex based on the reconstructed image of the pelvis portion.

3. The X-ray CT apparatus according to claim 2,
wherein the reconstruction calculator reconstructs a front image of the pelvis or an MPR image along a surface including the lower end of the pubis and the lower ends of the ischia on both sides, and
the sex estimation unit calculates a lower angle of the pubic bone based on a density value change between the born portion and the air in the front image or the MPR image and estimates a sex based on the lower angle of the pubic bone.

4. The X-ray CT apparatus according to claim 1,
wherein a site for which high-resolution scanning is performed is the lung field in a case where the death mode is death by drowning, and
the reconstruction calculator reconstructs at least a high-resolution image of the lung field and further includes a lung water amount estimation unit that measures a water volume in the lung based on the reconstructed image of the lung field.

5. The X-ray CT apparatus according to claim 1,
wherein sites of each injury or disease are at least included as a site for which high-resolution scanning is performed in a case where the death mode is head injury, thoracoabdominal injury, head disease, or heart disease, and
the reconstruction calculator reconstructs at least a high-resolution image of a site of the injury or disease.

6. The X-ray CT apparatus according to claim 1,
wherein the reconstruction calculator reconstructs a blood vessel image of a specified position, and
a blood vessel rupture position estimation unit that estimates a rupture position in a blood vessel based on the reconstructed blood vessel image is further included.

7. The X-ray CT apparatus according to claim 6,
wherein the blood vessel rupture position estimation unit extracts a leakage region of blood using the region growing process that sets an arbitrary point inside a blood vessel as a start point and estimates a rupture position in a blood vessel based on a CT value difference between the leaked blood and the blood in the blood vessel.

8. A scanning method comprising:
displaying options of a death mode on a display device of an X-ray CT apparatus;
reading scanning conditions according to the death mode selected from the options by an operator from a storage unit of the X-ray CT apparatus where the scanning conditions according to the death mode are stored in advance;
scanning using the X-ray CT apparatus according to the read scanning conditions; and
using transmission X-ray data acquired during the scanning in order to reconstruct an image according to the death mode by the X-ray CT apparatus
wherein death by fire, death by drowning, head injury, thoracoabdominal injury, head disease, heart disease, and the others are included as the displaying options of the death mode, and
a site for high-resolution scanning and recommended scanning conditions for the said site according to each death mode are included in the scanning conditions in addition to recommended scanning conditions for performing standard scanning for the whole body.

9. An X-ray CT apparatus comprising:
an X-ray source that generates an X-ray;
an X-ray detector that detects an X-ray transmitted through an object;
a data acquisition system that acquires data of the transmitted X-ray detected by the X-ray detector;

a storage unit that stores scanning conditions according to a death mode;

an input unit that allows an operator to select the death mode;

a scanning controller that reads scanning conditions according to the selected death mode from the storage unit and scanning according to the read scanning conditions; and a reconstruction calculator that reconstructs an image according to the death mode using the transmission X-ray data acquired from the data acquisition system during scanning;

wherein sites of each injury or disease are at least included as a site for which high-resolution scanning is performed in a case where the death mode is head injury, thoracoabdominal injury, head disease, or heart disease, and the reconstruction calculator reconstructs at least a high-resolution image of a site of the injury or disease.

* * * * *